United States Patent
Alghamdi et al.

(10) Patent No.: US 12,142,078 B2
(45) Date of Patent: Nov. 12, 2024

(54) EMOTION RECOGNITION AND NOTIFICATION SYSTEM

(71) Applicants: Abdullah Alghamdi, Najran (SA); Asadullah Shaikh, Najran (SA); Mohammad Tabrez Quasim, Bisha (SA); Mesfer Alrizq, Najran (SA); Surbhi Bhatia, Hofuf (SA); Mana Saleh Al Reshan, Najran (SA); Shadab Alam, Jizan (SA)

(72) Inventors: Abdullah Alghamdi, Najran (SA); Asadullah Shaikh, Najran (SA); Mohammad Tabrez Quasim, Bisha (SA); Mesfer Alrizq, Najran (SA); Surbhi Bhatia, Hofuf (SA); Mana Saleh Al Reshan, Najran (SA); Shadab Alam, Jizan (SA)

(*) Notice: Subject to any disclaimer, the term of this patent is extended or adjusted under 35 U.S.C. 154(b) by 375 days.

(21) Appl. No.: 17/809,428

(22) Filed: Jun. 28, 2022

(65) Prior Publication Data
US 2022/0335752 A1   Oct. 20, 2022

(51) Int. Cl.
G06V 40/16 (2022.01)
A61B 5/00 (2006.01)
A61B 5/16 (2006.01)
G06V 10/82 (2022.01)

(52) U.S. Cl.
CPC ............ *G06V 40/174* (2022.01); *A61B 5/165* (2013.01); *A61B 5/74* (2013.01); *G06V 10/82* (2022.01); *G06V 40/165* (2022.01); *G06V 40/171* (2022.01)

(58) Field of Classification Search
CPC .... G06V 40/174; G06V 10/82; G06V 40/165; G06V 40/171; G06V 10/30; A61B 5/165; A61B 5/74
USPC ........................................................ 382/118
See application file for complete search history.

(56) References Cited

U.S. PATENT DOCUMENTS

| | | | |
|---|---|---|---|
| 2017/0238860 A1* | 8/2017 | El Kaliouby | .......... G16H 50/30 |
| 2018/0276454 A1* | 9/2018 | Han | ...................... G06V 40/171 |
| 2019/0251335 A1* | 8/2019 | Han | ...................... G06V 40/166 |
| 2020/0219295 A1* | 7/2020 | El Kaliouby | ........... G06T 11/00 |
| 2021/0307621 A1* | 10/2021 | Svenson | ................ A61B 5/015 |
| 2021/0326586 A1* | 10/2021 | Sorci | ...................... G16H 15/00 |
| 2022/0121884 A1* | 4/2022 | Zadeh | .................... G06N 3/006 |

\* cited by examiner

*Primary Examiner* — Ali Bayat
(74) *Attorney, Agent, or Firm* — Perilla Knox & Hildebrandt LLP; Kenneth A. Knox

(57) ABSTRACT

The present invention generally relates to an emotion recognition and notification system comprises an input unit includes a camera for capturing a facial image of a user's face; a pre-processing unit to remove noise and enhance the details of the captured facial image; a face detection unit to detect a face from the captured facial image; a features extraction unit to extract a set of image features from detected face from the captured facial image; a central processing unit equipped with a two channel facial expression recognition network based on CNN and LSTM to recognize an emotion of a user upon comparing the set of image features from a pre-stored image features; and a control unit equipped with a communication module to alert a registered user about a recognized emotion.

8 Claims, 1 Drawing Sheet

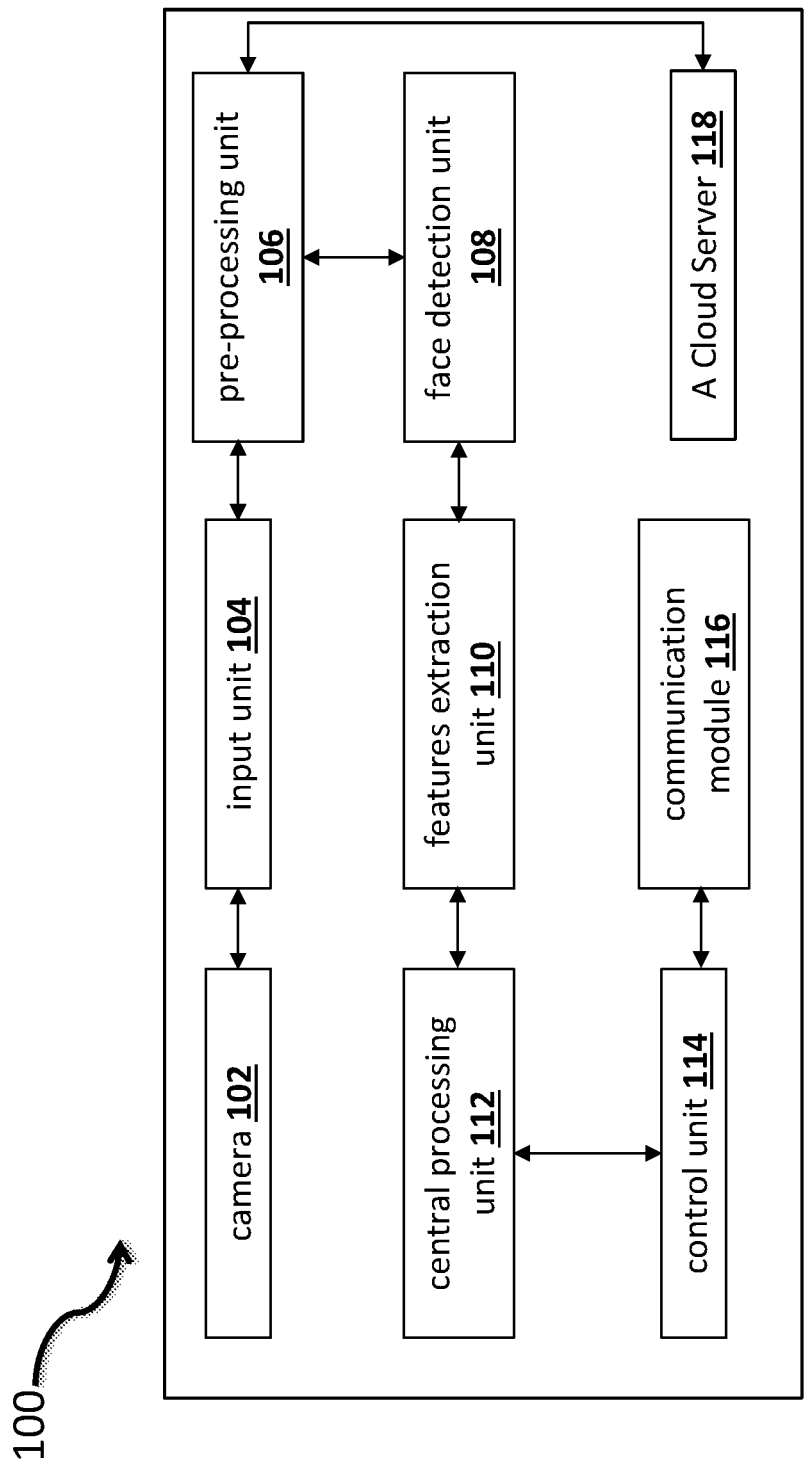

EMOTION RECOGNITION AND NOTIFICATION SYSTEM

FIELD OF THE INVENTION

The present disclosure relates to computer vision processing technologies, and in particular, to an emotion recognition and notification system using computational techniques.

BACKGROUND OF THE INVENTION

Emotional recognition has drawn a lot of interest from academics both domestically and internationally as a significant research topic in the field of computer vision. Both expression recognition based on static photos and expression recognition based on video sequences are now used in the recognition of facial expressions. To extract static expression characteristics from a single facial expression image is the main goal of facial expression analysis based on static photos. The static and dynamic elements of the expression sequence are combined to analyse the emotional state of the persons in the video. These two techniques now have a high recognition rate and generalisation capacity for facial expression recognition. Therefore, to conduct face emotional identification, the current patent employs the single-frame static picture of the facial expression data set and the information aspects of the expression sequence.

The manual extraction of facial characteristics is a stage in the standard facial expression identification approach, but the features are only extracted once, the calculations are difficult, and the model's applicability is restricted. Recent years have seen a lot of interest in the scientific area of deep learning. Instead of the conventional method of manually selecting features, it combines multiple abstract data processing layers to create a computational model, allowing the machine to learn the features of data samples on its own while effectively avoiding the drawbacks of the conventional method of manually selecting features. Additionally, the deep learning approach uses a lot more data to learn the features than the conventional way of manually picking them, which might result in a fuller description of the feature information in the data. In summary, deep learning outperforms the conventional approach in terms of both accuracy and recognition time.

In the view of the forgoing discussion, it is clearly portrayed that there is a need to have an emotion recognition and notification system.

SUMMARY OF THE INVENTION

The present disclosure seeks to provide a facial features and expression-based emotion recognition and notification system using two channel facial expression recognition network.

In an embodiment, an emotion recognition and notification system is disclosed. The system includes an input unit includes a camera for capturing a facial image of a user's face. The system further includes a pre-processing unit to remove noise and enhance the details of the captured facial image. The system further includes a face detection unit to detect a face from the captured facial image. The system further includes a features extraction unit to extract a set of image features from detected face from the captured facial image. The system further includes a central processing unit equipped with a two channel facial expression recognition network based on CNN (Convolutional Neural Network) and LSTM (Long and Short Term Memory Network) to recognize an emotion of a user upon comparing the set of image features from a pre-stored image features, wherein the central processing unit executes a process for acquiring the recognition value corresponding to an expression of the face on the basis of differences between relative positions of pre-stored image features extracted from the face using an image previously received from the input unit at a timing when the input unit inputs an image, and relative positions derived in advance as references for the pre-stored image features extracted from one or more of the faces. The system further includes a control unit equipped with a communication module to alert a registered user about a recognized emotion.

In another embodiment, the set of image features are selected from a local feature including a pattern or distinct features including a point, edge, or small image patch, wherein the pre-stored image features are selected from a group of local feature including a pattern or distinct features including a point, edge, or small image patch configured with a group of expression classifications.

In another embodiment, a pre-stored image features is obtained upon pre-treating a plurality of facial expression sequence in a dataset, which includes tracking a face area of each of the plurality of images in the plurality of facial expression sequence through face detection tracking and cutting out a human face in the image, thereby generating the pretreated facial expression sequence; and processing the plurality of facial expression sequence into two facial expression sequences.

In another embodiment, the two-channel facial expression recognition network comprises a first channel and a second channel facial expression, wherein a last frame of the facial expression sequence with a first resolution is feeded into the first channel, and the facial expression sequence with the second resolution is feeded into the second channel, wherein either of the first resolution includes low resolution and the second resolution includes high resolution.

In another embodiment, the system comprises a training unit to train the two-channel facial expression recognition network based on CNN and LSTM using facial expression sequences with the two resolutions in the training set and the verification set into the first channel and the second channel.

In another embodiment, the emotions are selected a group of bored, excited, frantic, relaxed, surprise, fear, happiness, anger, neutral, sadness, disgust and the like.

In another embodiment, the set of image features detected from the user's face extracted from the captured image includes one or more of the skin texture appearance changes comprises one or more of the expression wrinkles, furrows, bulges, or illumination variations or a blushing, or multiple directional illumination conditions and multiple pose variations.

In another embodiment, the alert about a recognized emotion notifies the registered user including family members and hospital to help or assist the person of the recognized emotion.

An object of the present disclosure is to detect emotion of a person using its facial features and expression.

Another object of the present disclosure is to develop a two-channel facial expression recognition network for most appropriate facial emotion recognition.

Yet another object of the present invention is to deliver an expeditious and cost-effective emotion recognition and notification system to help and assist the person in need.

To further clarify advantages and features of the present disclosure, a more particular description of the invention will be rendered by reference to specific embodiments thereof, which is illustrated in the appended drawings. It is appreciated that these drawings depict only typical embodiments of the invention and are therefore not to be considered limiting of its scope. The invention will be described and explained with additional specificity and detail with the accompanying drawings.

BRIEF DESCRIPTION OF FIGURES

These and other features, aspects, and advantages of the present disclosure will become better understood when the following detailed description is read with reference to the accompanying drawings in which like characters represent like parts throughout the drawings, wherein:

FIG. 1 illustrates a block diagram of an emotion recognition and notification system in accordance with an embodiment of the present disclosure.

Further, skilled artisans will appreciate that elements in the drawings are illustrated for simplicity and may not have necessarily been drawn to scale. For example, the flow charts illustrate the method in terms of the most prominent steps involved to help to improve understanding of aspects of the present disclosure. Furthermore, in terms of the construction of the device, one or more components of the device may have been represented in the drawings by conventional symbols, and the drawings may show only those specific details that are pertinent to understanding the embodiments of the present disclosure so as not to obscure the drawings with details that will be readily apparent to those of ordinary skill in the art having benefit of the description herein.

DETAILED DESCRIPTION

For the purpose of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates.

It will be understood by those skilled in the art that the foregoing general description and the following detailed description are exemplary and explanatory of the invention and are not intended to be restrictive thereof.

Reference throughout this specification to "an aspect", "another aspect" or similar language means that a particular feature, structure, or characteristic described in connection with the embodiment is included in at least one embodiment of the present disclosure. Thus, appearances of the phrase "in an embodiment", "in another embodiment" and similar language throughout this specification may, but do not necessarily, all refer to the same embodiment.

The terms "comprises", "comprising", or any other variations thereof, are intended to cover a non-exclusive inclusion, such that a process or method that comprises a list of steps does not include only those steps but may include other steps not expressly listed or inherent to such process or method. Similarly, one or more devices or sub-systems or elements or structures or components proceeded by "comprises . . . a" does not, without more constraints, preclude the existence of other devices or other sub-systems or other elements or other structures or other components or additional devices or additional sub-systems or additional elements or additional structures or additional components.

Unless otherwise defined, all technical and scientific terms used herein have the same meaning as commonly understood by one of ordinary skill in the art to which this invention belongs. The system, methods, and examples provided herein are illustrative only and not intended to be limiting.

Embodiments of the present disclosure will be described below in detail with reference to the accompanying drawings.

Referring to FIG. 1, a block diagram of an emotion recognition and notification system is illustrated in accordance with an embodiment of the present disclosure. The system 100 includes an input unit 104 includes a camera 102 for capturing a facial image of a user's face, wherein a mobile camera may be selected for capturing a facial image, wherein image can be fed uploading an image on a user interface to recognize image of any person.

In an embodiment, a pre-processing unit 106 is connected to the input unit 104 to remove noise and enhance the details of the captured facial image.

In an embodiment, a face detection unit 108 is connected to the pre-processing unit 106 to detect a face from the captured facial image.

In an embodiment, a features extraction unit 110 is connected to the face detection unit 108 to extract a set of image features from detected face from the captured facial image.

In an embodiment, a central processing unit 112 is equipped with a two channel facial expression recognition network based on CNN (Convolutional Neural Network) and LSTM (Long and Short Term Memory Network) to recognize an emotion of a user upon comparing the set of image features from a pre-stored image features, wherein the central processing unit 112 executes a process for acquiring the recognition value corresponding to an expression of the face on the basis of differences between relative positions of pre-stored image features extracted from the face using an image previously received from the input unit 104 at a timing when the input unit 104 inputs an image, and relative positions derived in advance as references for the pre-stored image features extracted from one or more of the faces.

In an embodiment, a control unit 114 is equipped with a communication module 116 and connected to the central processing unit 112 to alert a registered user about a recognized emotion. The alert is received on a registered user computing device through the communication module 116.

In another embodiment, the set of image features are selected from a local feature including a pattern or distinct features including a point, edge, or small image patch, wherein the pre-stored image features are selected from a group of local feature including a pattern or distinct features including a point, edge, or small image patch configured with a group of expression classifications.

In another embodiment, a pre-stored image features is obtained upon pre-treating a plurality of facial expression sequence in a dataset, which includes tracking a face area of each of the plurality of images in the plurality of facial expression sequence through face detection tracking and cutting out a human face in the image, thereby generating the pretreated facial expression sequence; and processing the plurality of facial expression sequence into two facial expression sequences. The dataset is stored in a cloud server 118.

In another embodiment, the two-channel facial expression recognition network comprises a first channel and a second channel facial expression, wherein a last frame of the facial expression sequence with a first resolution is feeded into the first channel, and the facial expression sequence with the second resolution is feeded into the second channel, wherein either of the first resolution includes low resolution and the second resolution includes high resolution.

In another embodiment, a training unit is connected to the central processing unit 112 to train the two-channel facial expression recognition network based on CNN and LSTM using facial expression sequences with the two resolutions in the training set and the verification set into the first channel and the second channel.

In another embodiment, the emotions are selected a group of bored, excited, frantic, relaxed, surprise, fear, happiness, anger, neutral, sadness, disgust and the like.

In another embodiment, the set of image features detected from the user's face extracted from the captured image includes one or more of the skin texture appearance changes comprises one or more of the expression wrinkles, furrows, bulges, or illumination variations or a blushing, or multiple directional illumination conditions and multiple pose variations.

In another embodiment, the alert about a recognized emotion notifies the registered user including family members and hospital to help or assist the person of the recognized emotion.

The drawings and the forgoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions of any flow diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature or component of any or all the claims.

The invention claimed is:

1. An emotion recognition and notification system, the system comprises:
    an input unit includes a camera for capturing a facial image of a user's face;
    a pre-processing unit to remove noise and enhance the details of the captured facial image;
    a face detection unit to detect a face from the captured facial image;
    a features extraction unit to extract a set of image features from detected face from the captured facial image;
    a central processing unit equipped with a two channel facial expression recognition network based on CNN (Convolutional Neural Network) and LSTM (Long and Short Term Memory Network) to recognize an emotion of a user upon comparing the set of image features from a pre-stored image features, wherein the central processing unit executes a process for acquiring the recognition value corresponding to an expression of the face on the basis of differences between relative positions of pre-stored image features extracted from the face using an image previously received from the input unit at a timing when the input unit inputs an image, and relative positions derived in advance as references for the pre-stored image features extracted from one or more of the faces; and
    a control unit equipped with a communication module to alert a registered user about a recognized emotion.

2. The system as claimed in claim 1, wherein the set of image features are selected from a local feature including a pattern or distinct features including a point, edge, or small image patch, wherein the pre-stored image features are selected from a group of local feature including a pattern or distinct features including a point, edge, or small image patch configured with a group of expression classifications.

3. The system as claimed in claim 1, wherein a pre-stored image features is obtained upon pre-treating a plurality of facial expression sequence in a dataset, which includes tracking a face area of each of the plurality of images in the plurality of facial expression sequence through face detection tracking and cutting out a human face in the image, thereby generating the pretreated facial expression sequence; and processing the plurality of facial expression sequence into two facial expression sequences.

4. The system as claimed in claim 1, wherein the two-channel facial expression recognition network comprises a first channel and a second channel facial expression, wherein a last frame of the facial expression sequence with a first resolution is feeded into the first channel, and the facial expression sequence with the second resolution is feeded into the second channel, wherein either of the first resolution includes low resolution and the second resolution includes high resolution.

5. The system as claimed in claim 4, wherein said system comprises a training unit to train the two-channel facial expression recognition network based on CNN and LSTM using facial expression sequences with the two resolutions in the training set and the verification set into the first channel and the second channel.

6. The system as claimed in claim 1, wherein the emotions are selected a group of bored, excited, frantic, relaxed, surprise, fear, happiness, anger, neutral, sadness, disgust and the like.

7. The system as claimed in claim 1, wherein the set of image features detected from the user's face extracted from the captured image includes one or more of the skin texture appearance changes comprises one or more of the expression wrinkles, furrows, bulges, or illumination variations or a blushing, or multiple directional illumination conditions and multiple pose variations.

8. The system as claimed in claim 1, wherein the alert about a recognized emotion notifies the registered user including family members and hospital to help or assist the person of the recognized emotion.

* * * * *